United States Patent
Skoletsky et al.

(10) Patent No.: US 11,419,505 B2
(45) Date of Patent: Aug. 23, 2022

(54) EARLY DETECTION AND TREATMENT OF VASCULAR DYSFUNCTION USING STIMULATION TOGETHER WITH CAPILLARY BLOOD FLOW MONITORING

(71) Applicant: Dermaflow LLC, Moorestown, NJ (US)

(72) Inventors: Ilya Skoletsky, Beer Sheva (IL); Irene Jaffe, Yavne (IL)

(73) Assignee: DERMAFLOW LLC, Moorestown, NJ (US)

( * ) Notice: Subject to any disclaimer, the term of this patent is extended or adjusted under 35 U.S.C. 154(b) by 304 days.

(21) Appl. No.: 16/758,658

(22) PCT Filed: Nov. 1, 2018

(86) PCT No.: PCT/US2018/058708
§ 371 (c)(1),
(2) Date: Apr. 23, 2020

(87) PCT Pub. No.: WO2019/089924
PCT Pub. Date: May 9, 2019

(65) Prior Publication Data
US 2020/0345242 A1 Nov. 5, 2020

Related U.S. Application Data

(60) Provisional application No. 62/581,236, filed on Nov. 3, 2017.

(51) Int. Cl.
*A61B 5/02* (2006.01)
*A61B 5/0205* (2006.01)
(Continued)

(52) U.S. Cl.
CPC .......... *A61B 5/02055* (2013.01); *A61B 5/026* (2013.01); *A61B 5/4836* (2013.01);
(Continued)

(58) Field of Classification Search
None
See application file for complete search history.

(56) References Cited

U.S. PATENT DOCUMENTS 8,551,008 B2 10/2013 Naghavi et al.
2008/0097558 A1 4/2008 Eggers et al.
(Continued)

FOREIGN PATENT DOCUMENTS

JP 2012519902 A 8/2012

OTHER PUBLICATIONS

International Search Report and Written Opinion, PCT/US2018/058708, dated Mar. 29, 2019 (8 pp.).

*Primary Examiner* — Ankit D Tejani
(74) *Attorney, Agent, or Firm* — Eversheds Sutherland (US) LLP

(57) ABSTRACT

The combination of skin-contacted stimulation together with capillary blood flow monitoring is applied in a tandem, coordinated fashion in an integrated system and method to provide early detection of compromised circulation conditions, to provide data useful for prescribing therapeutic treatments including stimulation therapies, and to monitor the effectiveness of various treatments. The disclosed methods and system can apply to a broad spectrum of diagnosed and/or undiagnosed vascular diseases and extend to detection and treatment of limb or appendage injury. An integrated device which can be a portable or a wearable product which makes use of the new system and method is disclosed.

25 Claims, 3 Drawing Sheets

(51) Int. Cl.
  *A61B 5/026* (2006.01)
  *A61B 5/00* (2006.01)
  *A61F 7/00* (2006.01)
  *A61H 23/00* (2006.01)
  *A61N 1/04* (2006.01)
  *A61N 2/00* (2006.01)
  *A61N 5/06* (2006.01)
  *A61N 7/00* (2006.01)

(52) U.S. Cl.
  CPC .............. *A61B 5/7257* (2013.01); *A61F 7/00* (2013.01); *A61H 23/00* (2013.01); *A61N 1/0456* (2013.01); *A61N 2/002* (2013.01); *A61N 5/0613* (2013.01); *A61N 7/00* (2013.01); *A61F 2007/0001* (2013.01); *A61F 2007/0095* (2013.01); *A61N 2005/0659* (2013.01); *A61N 2007/0004* (2013.01)

(56) References Cited

U.S. PATENT DOCUMENTS

| | | |
|---|---|---|
| 2013/0053655 A1 | 2/2013 | Castellanos |
| 2013/0218034 A1 | 8/2013 | Bowman et al. |

EARLY DETECTION AND TREATMENT OF VASCULAR DYSFUNCTION USING STIMULATION TOGETHER WITH CAPILLARY BLOOD FLOW MONITORING

CROSS REFERENCE TO RELATED APPLICATIONS

This application is a 35 U.S.C. § 371 National stage application of International Patent Application No. PCT/US2018/058708, filed Nov. 1, 2018, which claims the benefit of priority to U.S. Provisional Patent Application No. 62/581,236, filed Nov. 3, 2017, each of which is incorporated herein by reference in its entirety.

TECHNICAL FIELD

This disclosure relates to methods and systems for detecting and treating or preventing vascular dysfunction.

BACKGROUND OF THE INVENTION

Peripheral arterial disease (PAD) affects approximately 8-12 million Americans and roughly 150 million people worldwide. Advanced age of the patient can significantly exacerbate this disease, as does limited mobility in general. It has been estimated that at least 20% of the symptomatic patients with PAD have diabetes, the latter imparting a significantly heightened risk for lower limb amputation. Even for the asymptomatic patient, PAD is a marker for systemic vascular diseases involving coronary, cerebral, and renal vessels, which can lead to an elevated risk of myocardial infarction (MI), stroke, and death.

In addition to compromised blood flow due to disease or conditions developed as a result of unhealthy lifestyle and/or genetics, injury to the lower limbs can also result in "temporary" compromised blood flow to the injured muscle. This occurs very often with athletes and in sports related activities. Unfortunately, both athletes and non-athlete populations often return to full activity or full mobility without proper healing, which can exacerbate the injury even further causing medical complications.

Therefore, what are needed are better systems and methods for providing early detection of vascular dysfunction including lower limb vascular insufficiency, better systems and methods for monitoring compromised blood flow due to injury, and better methods of stimulating circulation to improve vascular function. Such systems and methods could lead the way to major improvements in healthcare as well as significant cost savings for consumers, healthcare institutions, and insurers.

BRIEF SUMMARY OF THE INVENTION

This disclosure describes methods, systems, and devices for detecting vascular insufficiencies in upper or lower extremities of a subject, including early detection of vascular insufficiencies, and further provides methods, systems, and devices for treating vascular insufficiencies. In an aspect, this disclosure provides for the identifiable trends and patterns to detect early vascular insufficiencies, which can be generated through simultaneous peripheral blood flow monitoring and stimulation such as electrical stimulation, infrared stimulation, ultrasound stimulation, and the like. One aspect is provided by applying a stimulation while monitoring and determining a capillary blood flow (CBF) response to the stimulation in an upper or lower extremity.

According to an aspect, the tandem, coordinated, or integrated use of a stimulatory modality in combination with a capillary blood flow module or system applied to the skin of the upper or lower extremities can be used for detection of vascular insufficiencies. This tandem or integrated use of a stimulatory modality can provide a monitoring technology which can detect changes in the peripheral blood flow including early detection. In a further aspect, the stimulatory mode of the same system can be used post-detection for the treatment of the vascular insufficiency to facilitate peripheral blood flow (also known as capillary blood flow or CBF).

In an aspect, there is provided a method for detecting vascular dysfunction in an extremity of a human body, in which the method can comprise:
  a) providing a capillary blood flow sensor comprising:
    i) a heater for applying heat to an area of skin to change the temperature of the skin from a first temperature to a second temperature and for maintaining a constant temperature gradient between the first and second temperatures, and a power source for providing a power to the heater; and
    ii) a temperature sensor for measuring the first temperature at the area of skin;
  b) determining a capillary blood flow response to a stimulation in an upper or lower extremity by:
    i) in the absence of the stimulation, measuring a first temperature at an area of skin with the temperature sensor;
    ii) applying heat to the area of skin with the heater to change the first temperature to a second temperature and maintaining the temperature gradient constant;
    iii) measuring the heater power dissipation required to maintain the temperature gradient constant;
    iv) determining a baseline capillary blood flow as a function of the heater power dissipation based upon a linear relationship of the Fourier equation;
    v) applying the stimulation at two or more different stimulation intensities at the area of skin and determining two or more corresponding stimulated capillary blood flows as a function of the heater power dissipation based upon the linear relationship of the Fourier equation; and
  c) comparing the baseline capillary blood flow to each of the two or more stimulated capillary blood flows and determining a change in capillary blood flow as a function of the corresponding stimulation intensity to detect vascular dysfunction in the upper or lower extremity.

The stimulation is applied at two or more different stimulation intensities to determine two or more corresponding stimulated capillary blood flows, because it is the trend in the stimulated capillary blood flows as a function of stimulation intensity that is diagnostic of disease or injury in the disclosed methods.

In embodiments, more than two stimulation intensities are used and changes in capillary blood flow as a function of stimulation intensity are measured. In some embodiments, applying the stimulation at two or more different stimulation intensities occurs in an increasing stimulation intensity order, that is, capillary blood flow measurements are carried out in order of increasing stimulation intensity.

While many different types of stimulations may be used with the capillary blood flow sensor in the manner disclosed, such as electrical stimulation, magnetic stimulation, infrared stimulation, ultrasound stimulation, and the like, the stimulation can also comprise transcutaneous electrical neural stimulation (TENS).

In accordance with a further aspect, there is provided a method for treating vascular dysfunction in an extremity of a human body, in which the method can comprise:

a) providing a capillary blood flow sensor comprising:
   i) a heater for applying heat to an area of skin to change the temperature of the skin from a first temperature to a second temperature and for maintaining a constant temperature gradient between the first and second temperatures, and a power source for providing a power to the heater; and
   ii) a temperature sensor for measuring the first temperature at the area of skin;
b) determining a capillary blood flow response to a first stimulation in an upper or lower extremity by:
   i) in the absence of the first stimulation, measuring a first temperature at an area of skin with the temperature sensor;
   ii) applying heat to the area of skin with the heater to change the first temperature to a second temperature and maintaining the temperature gradient constant;
   iii) measuring the heater power dissipation required to maintain the temperature gradient constant;
   iv) determining a baseline capillary blood flow as a function of the heater power dissipation based upon a linear relationship of the Fourier equation;
   v) applying the first stimulation at two or more different first stimulation intensities at the area of skin and determining two or more corresponding stimulated capillary blood flows as a function of the heater power dissipation based upon the linear relationship of the Fourier equation;
c) comparing the baseline capillary blood flow to each of the two or more stimulated capillary blood flows and determining a change in capillary blood flow as a function of the corresponding first stimulation intensity to detect vascular dysfunction in the upper or lower extremity; and
d) treating the vascular dysfunction if detected, for example by applying a second stimulation, or preventing the vascular dysfunction if not detected, for example by applying a second stimulation.

Again, the first (diagnostic) stimulation is applied at two or more different stimulation intensities to determine two or more corresponding stimulated capillary blood flows, because it is the trend in the stimulated capillary blood flows as a function of stimulation intensity that is diagnostic of disease or injury.

In an aspect, the step of treating the vascular dysfunction can comprise utilizing a stimulation treatment regimen of applying the second stimulation one or more times to the upper or lower extremity at one or more selected second stimulation intensities, for one or more durations of time, in which the second (treatment) stimulation type is the same as the first (diagnostic) stimulation type, or in which the second (treatment) stimulation type is different from the first (diagnostic) stimulation type.

In a further aspect, this disclosure provides a system for detecting vascular dysfunction in an extremity of a human body, in which the system can comprise a capillary blood flow module and a stimulation module, wherein a) the capillary blood flow module comprises:
   i) a heater for applying heat to an area of skin to change the temperature of the skin from a first temperature to a second temperature and for maintaining a constant temperature gradient between the first and second temperatures, and a power source for providing power to the heater;
   ii) a temperature sensor for measuring temperature at the area of skin, for example for measuring the first temperature at the area of skin;
   iii) a controller in communication with the heater and the temperature sensor which [A] operates the heater for maintaining the temperature gradient constant and [B] operates the temperature sensor in a first operative mode and a second operative mode, wherein
      in the first operative mode the temperature sensor measures the first temperature at the area of skin,
      and wherein in the second operative mode, the controller operates the heater to maintain the temperature gradient constant between the first and second temperatures;
   and
   iv) a processor in communication with the controller for determining capillary blood flow units corresponding to the measured first temperature and the heater power required to maintain the temperature gradient constant; and
b) the stimulation module comprises:
   i) an electrical current waveform generator for generating an electrical stimulation signal;
   ii) a controller for regulating the intensity of the electrical stimulation signal in communication with the electrical current waveform generator; and
   iii) at least one electrode and at least one lead, each lead in communication with the controller and a corresponding electrode.

According to this aspect, the capillary blood flow module controller and the stimulation module controller can operate in tandem, coordinated, or integrated fashion to detect vascular dysfunction. In an aspect, for example, the capillary blood flow module controller and the stimulation module controller can be under independent control if desired, but they can be configured to be used in a synergistic fashion to detect vascular dysfunction according to this disclosure. Moreover, the functionality of the capillary blood flow module controller and the stimulation module controller can be integrated into single operating system if desired.

Therefore, this disclosure also provides a computer, in which the computer can comprise a processor; and a non-transitory computer recordable storage medium in communication with the processor, the non-transitory computer recordable storage medium storing program code, which when executed by the processor, performs a computer-implemented processes as described above. As understood by the person of ordinary skill, this disclosure provides for algorithms based on our detected, diagnostic patterns, which can provide information on whether an extremity is diseased or not. For example, in some aspects, two, three, four, five, six, seven, eight, nine, ten, or more stimulation intensities can be used and changes in capillary blood flow can be measured, and the trend in capillary blood flow as a function of intensity can be analyzed using various algorithms to provide a quantitative measure of the extent of disease.

According to a further aspect, this disclosure provides a system for detecting and treating vascular dysfunction in an extremity of a human body, in which the system can comprise a capillary blood flow module and a stimulation module, wherein a) the capillary blood flow module comprises:
   i) a heater for applying heat to an area of skin to change the temperature of the skin from a first temperature to a second temperature and for maintaining a constant temperature gradient between the first and second temperatures, and a power source for providing power to the heater;

ii) a temperature sensor for measuring temperature at the area of skin, for example for measuring the first temperature at the area of skin;

iii) a controller in communication with the heater and the temperature sensor which [A] operates the heater for maintaining the temperature gradient constant and [B] operates the temperature sensor in a first operative mode and a second operative mode, wherein in the first operative mode the temperature sensor measures the first temperature at the area of skin, and wherein in the second operative mode, the controller operates the heater to maintain the temperature gradient constant between the first and second temperatures;

and iv) a processor in communication with the controller for determining capillary blood flow units corresponding to the measured first temperature and the heater power required to maintain the temperature gradient constant; and b) the stimulation module comprises:

i) an electrical current waveform generator for generating an electrical stimulation signal;

ii) a controller for regulating the intensity of the electrical stimulation signal in communication with the electrical current waveform generator; and iii) at least one electrode and at least one lead, each lead in communication with the controller and a corresponding electrode;

wherein the stimulation module can operate in tandem with the capillary blood flow module to detect vascular dysfunction. That is, they can be under independent control if desired, but can be configured to be used in a synergistic fashion to detect vascular dysfunction according to this disclosure.

These and other aspects and embodiments of the disclosure are set out in the figures, examples, and detailed description below. Additional features or variations thereof can be provided in addition to those set forth herein, such as for example, various feature combinations and sub-combinations of these described in the detailed description.

BRIEF DESCRIPTION OF THE DRAWINGS

FIG. 3 illustrates a plot of the time of the measurement in minutes using the Veino Plus™ Sport electrical stimulator (x-axis) versus the relative change in peripheral blood flow rate. Power and therefore intensity are kept constant in this test, and no changes in frequency (bpm) are employed. The capillary blood flow along the y-axis of FIG. 3 is a relative scale. Data were collected following a muscle injury at two days after the injury (bottom plot, lower relative flow rate) and at three days after the injury (top plot, higher relative flow rate). The day 2 data (bottom line) show a diminishing capillary blood flow trend with increasing time. The day 3 data (top line) demonstrate an increasing capillary blood flow trend with increasing time, providing evidence of healing as the capillary blood flow at day 3 as reflected in this increasing capillary blood flow trend suggesting a more healthy tissue resulting from the healing progression at day 3.

DETAILED DESCRIPTION

Figure 1:
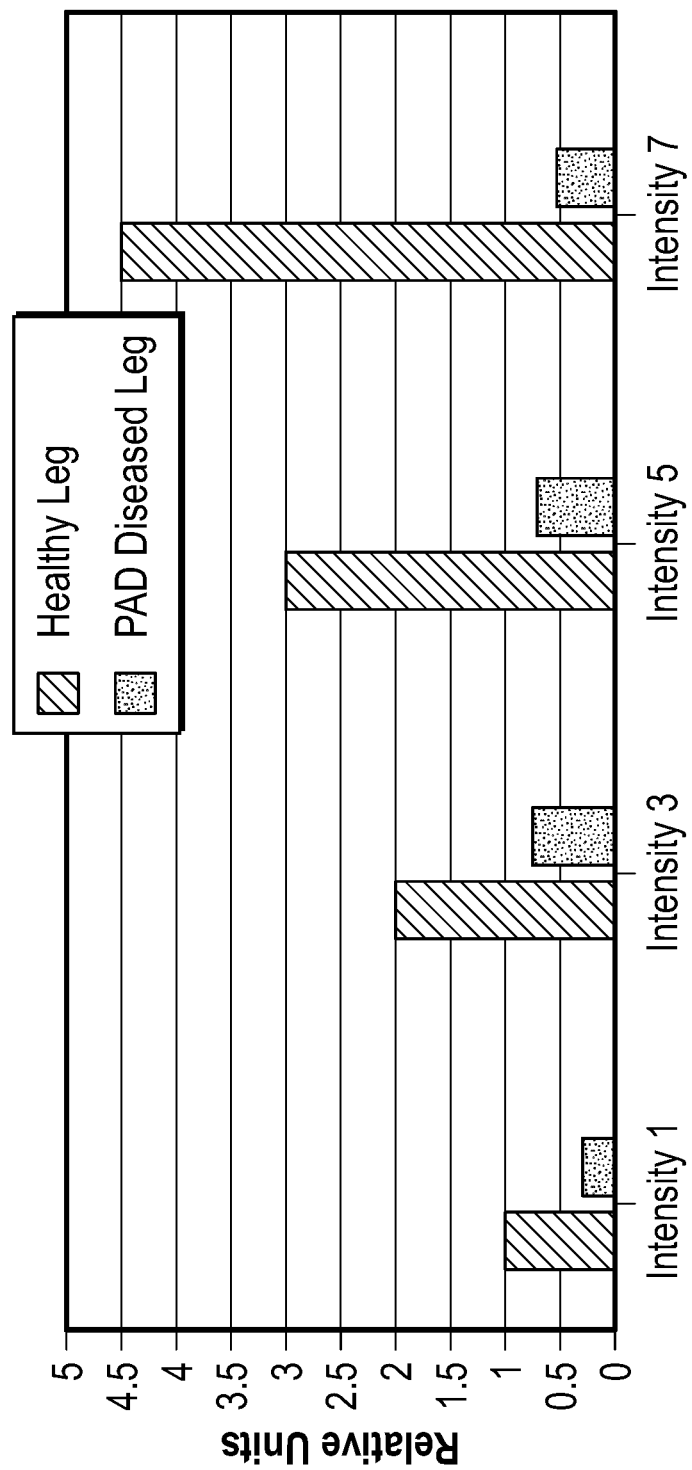
FIG. 1 illustrates an embodiment of the disclosure and plots the stimulation intensity versus the change in peripheral blood flow rate using transcutaneous electrical neural stimulation (TENS) as the stimulation method. The data were measured on the calf muscle of the legs of different human subjects and illustrate how the difference between baseline capillary blood flow and the stimulated capillary blood flows vary in relative units, as a function of the corresponding stimulation intensity in a healthy leg versus a Peripheral Arterial Diseased (PAD) leg. The intensity level of a Trans-Cutaneous Electronic Neural Stimulation (Omron E2 Elite) is shown along the x-axis.

According to aspects of this disclosure, provided herein are methods, systems, and devices for detecting vascular insufficiencies, and further provides methods, systems, and devices for treating vascular insufficiencies. Early detection of vascular insufficiencies resulting in dysfunction are also provided by the methods, systems, and devices according to this disclosure. In an aspect, this disclosure provides for the identifiable trends and patterns to detect early vascular insufficiencies, which can be generated through simultaneous peripheral blood flow monitoring and stimulation such as electrical stimulation, magnetic stimulation, infrared stimulation, ultrasound stimulation, and the like. One aspect is provided by applying a stimulation while monitoring and determining a capillary blood flow response to the stimulation in an upper or lower extremity.

Definitions. To define more clearly the terms used herein, the following definitions are provided, and unless otherwise indicated, the following definitions are applicable to this disclosure. If a term is used in this disclosure but is not specifically defined herein, the definition from the *Academic Press Dictionary of Science and Technology*, ed. C. Morris, Academic Press, Inc.; San Diego, c. 1992, can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

While devices and methods are described in terms of "comprising" various components or steps, the compositions and methods can also "consist essentially of" or "consist of" the various components or steps, unless stated otherwise. The terms "including", "with", and "having", as used herein, are defined as comprising (i.e., open language), unless specified otherwise.

The term "capillary blood flow sensor" refers to the combination of [1] a heater or heating means for heating a surface or an area of a surface, including skin, and for applying and maintaining a constant predetermined temperature gradient, and [2] a temperature sensor or temperature sensing element for measuring temperature, whether this combination is physically attached or not. When the combination of a heater and a temperature sensor are physically combined or attached into a single unit, the single unit can be referred to as a "capillary blood flow sensor module" or simply, "sensor module." Typically, the heater and the temperature sensor are combined into a single, thermally insulated capillary blood flow sensor module, which can be thermally insulated on the portions of the sensor module unit that are not in contact with the skin or the surface to be heated and measured. In this disclosure, reference to a "sensor" or a "sensor module" can include the other, unless the context requires otherwise. Aspects of the capillary blood flow sensor, its construction, use, and calibration are disclosed in U.S. Pat. No. 6,221,025 and PCT Patent Application No. PCT/US2018/044369, each of which is incorporated herein in its entirety.

Regarding the "sensor" and the "sensor module" of this disclosure with respect to the capillary blood flow device, the sensor and sensor module can further include other elements in addition to the heater and temperature sensor for measuring various parameters at the skin, for providing various stimuli to the skin, or for carrying out any number of other functions. This is particularly useful in the sensor module, which if desired can further include, for example, an accelerometer, a heart rate sensor, an oxygen saturation or blood oxygen sensor, a blood pressure sensor, and the like, including any combinations thereof. In this manner, the sensor module provides a convenient way of measuring several parameters while in contact with the skin.

Terms such as "controller", "processor", and the like, refer to the electronic means by which the various functions of the devices and methods disclosed herein are carried out. The controller, processor, and the like, can be combined into a single device or computer, or they can be separated into individual electronic devices or sub-combinations of electronic devices, as well understood by the person of ordinary skill in the relevant art. The controller is the structure that functions to control, the processor is the structure that carries out the processing function, and the calibrating unit is the structure that carries out the calibration function, and these structures can be the same or can be different. These may also be referred to herein as a control means, a processing means, and a calibrating means.

Numerical ranges are disclosed herein. When a range of any type is disclosed or claimed, Applicant's intent is to disclose or claim individually each possible number that such a range could reasonably encompass, including end points of the range as well as any sub-ranges and combinations of sub-ranges encompassed therein, unless otherwise specified. For example, by disclosing a temperature of from 30° C. to 40° C., Applicant's intent is to recite individually, 30° C., 31° C., 32° C., 33° C., 34° C., 35° C., 36° C., 37° C., 38° C., 39° C., and 40° C., including any sub-ranges and combinations of sub-ranges encompassed therein, and these methods of describing such ranges are interchangeable. Moreover, all numerical end points of ranges disclosed herein are approximate, unless excluded by proviso. As a representative example, if a temperature is disclosed in a range of from 30° C. to 40° C., this range should be interpreted as encompassing temperatures in a range from "about" 30° C. to "about" 40° C. Applicant reserves the right to proviso out or exclude any individual members of any such group of values or ranges, including any sub-ranges or combinations of sub-ranges within the group, that can be claimed according to a range or in any similar manner, if for any reason Applicants choose to claim less than the full measure of the disclosure, for example, to account for a reference that Applicants can be unaware of at the time of the filing of the application.

Values or ranges may be expressed herein as "about" a particular value. When such values or ranges are expressed, other embodiments disclosed include the specific value recited. Similarly, when values are expressed as approximations, by use of the antecedent "about," it will be understood that the particular value forms another embodiment. In another aspect, use of the term "about" can mean ±20% of the stated value, ±15% of the stated value, ±10% of the stated value, ±5% of the stated value, or ±3% of the stated value.

The term "near zero" as it relates to determining the slope of the change in capillary blood flow versus stimulation intensity trend line is defined herein as a slope of 0.00 (zero), about 0.00, about ±0.01, about ±0.02, about ±0.05, about ±0.10, or about ±0.15. In embodiments, the term "near zero" slope means a slope of 0.00 (zero), about 0.00, about ±0.01, about ±0.02, about ±0.05, about ±0.10, or about ±0.15, when plotted according to the conditions of Examples 1 and 2. In determining whether the slope of a change in capillary blood flow versus stimulation intensity trend line is zero or near-zero, the increase or decrease in slope is measured for the linear best fit over three or more stimulation intensity measurements, four or more stimulation intensity measurements, five or more stimulation intensity measurements, six or more stimulation intensity measurements, seven or more stimulation intensity measurements, eight or more stimulation intensity measurements, nine or more stimulation intensity measurements, ten or more stimulation intensity measurements, 11 or more stimulation intensity measurements, or 12 or more stimulation intensity measurements.

The terms "continuously increasing", "continuously increasing with increasing stimulation", and the like as they relate to determining the slope of the change in capillary blood flow versus stimulation intensity trend line means that a positive slope in the trend line is measured between each set of adjacent stimulation intensity measurements for three or more stimulation intensities. Alternatively, the slope can be measured between each adjacent stimulation intensity measurement for four or more stimulation intensities, five or more stimulation intensities, six or more stimulation intensities, seven or more stimulation intensities, eight or more stimulation intensities, nine or more stimulation intensities, ten or more stimulation intensities, 11 or more stimulation intensities, or 12 or more stimulation intensities. For example, if four different intensity measurements are taken, the slope is "continuously increasing" if the slope of the trend line between each of measurements 1 and 2, measurements 2 and 3, and measurements 3 and 4 are all positive.

Similarly, the terms "not continuously increasing", "not continuously increasing with increasing stimulation", and the like as they relate to determining the slope of the change in capillary blood flow versus stimulation intensity trend line means that a positive slope in the trend line is not measured between each set of adjacent stimulation intensity measurements for three or more stimulation intensities. Alternatively, the slope can be measured between each adjacent stimulation intensity measurement for four or more stimulation intensities, five or more stimulation intensities, six or more stimulation intensities, seven or more stimulation intensities, eight or more stimulation intensities, nine or more stimulation intensities, ten or more stimulation intensities, 11 or more stimulation intensities, or 12 or more stimulation intensities. For example, if four different intensity measurements are taken, the slope is "not continuously increasing" if the slope of the trend line between each of measurements 1 and 2, measurements 2 and 3, and measurements 3 and 4 are not all positive.

The terms "continuously decreasing", "continuously decreasing with increasing stimulation", and the like as they relate to determining the slope of the change in capillary blood flow versus stimulation intensity trend line means that a zero or negative slope in the trend line is measured between each set of adjacent stimulation intensity measurements for three or more stimulation intensities. Alternatively, the slope can be measured between each adjacent stimulation intensity measurement for four or more stimulation intensities, five or more stimulation intensities, six or more stimulation intensities, seven or more stimulation intensities, eight or more stimulation intensities, nine or more stimulation intensities, ten or more stimulation intensities, 11 or more stimulation intensities, or 12 or more stimulation intensities. For example, if four different intensity measurements are taken, the slope is "continuously decreasing" if the slope of the trend line between each of measurements 1 and 2, measurements 2 and 3, and measurements 3 and 4 are all zero or negative.

All publications and patents mentioned herein are incorporated herein by reference for the purpose of describing and disclosing, for example, the constructs and methodologies which can be used in connection with the presently described devices and methods. The publications discussed throughout the text are provided solely for their disclosure prior to the filing date of the present application. Nothing herein is to be construed as an admission that the inventors are not entitled to antedate such references.

Various forms or methods of vascular blood flow "stimulation" are reported to impact or influence capillary blood flow as the stimulation is applied on or through the skin. Such methods include but are not limited to electrical, magnetic, infrared, ultrasound, mechanical vibration stimulation, thermal changes (heat and/or cold) stimulation methods. Many readily available and over-the-counter devices based upon these technologies claim to directly or indirectly increase the peripheral blood flow circulation. Certain research studies have demonstrated correlations between these stimulation technology treatments and an increase in the peripheral blood flow in the capillaries. See, for example, the following references, each of which is incorporated herein by reference in its entirety:

1. Effects of electrical stimulation therapy on the blood flow in chronic critical limb ischemia patients following regenerative therapy; S. Yamabata, H. Shiraishi, M. Munechika, H. Fukushima, Y. Fukuoka, T. Hojo, T. Shirayama, M. Horii, S. Matoba, and T. Kubo; *J Manipulative Physiol. Ther.* 2015, 38(3) (March-April), 195-202;
2. Effects of alternating magnetic fields and low-frequency electric currents on human skin blood flow; S. Ueno, P. Lövsund, and P. Å. Öberg; *Medical and Biological Engineering and Computing* 1986, 24(1) (January), 57-61;
3. Static magnetic fields induce blood flow decrease and platelet adherence in tumor microvessels; S. Strieth, D. Strelczyk, M. E. Eichhorn, M. Dellian, S. Luedemann, J. Griebel, M. Bellemann, A. Berghaus, and G. Brix; *Cancer Biology & Therapy* 2008, 7(6), 814-819;
4. Far-infrared rays (FIR) and infrared rays (IR) generate heat and were claimed to be benefit to wound healing. We compare the differences of light penetration and human skin blood flow between FIR and IR irradiation, C.-D. Lin, C.-C. Huang, C.-H. Chen, T.-W. Wong, M.-S. Young; *Biophotonics* 2004, APBP 2004. The Second Asian and Pacific Rim Symposium;
5. Biological effect of far-infrared therapy on increasing skin microcirculation in rats; S.-Y. Yu, J.-H. Chiu, S.-D. Yang, Y.-C. Hsu, W.-Y. Lui, C.-W. Wu; *Photodermatol. Photoimmunol. Photomed.* 2006, 22, 78-86;
6. Effects of therapeutic ultrasound on intramuscular blood circulation and oxygen dynamics; K. Morishita, H. Karasuno, Y. Yokoi, K. Morozumi, H. Ogiharam, T. Ito, T. Fujiwara, T. Fujimoto, K. Abe; *J. Jpn. Phys. Ther. Assoc.* 2014, 17(1), 1-7;
7. Therapeutic ultrasound: the effects upon cutaneous blood flow in humans; J. G. Noble, V. Lee, F. Griffith-Noble; *Ultrasound Med. Biol.* 2007, 33(2) (February), 279-85;
8. The effect of multidirectional mechanical vibration on peripheral circulation of humans; C. Button, N. Anderson, C. Bradford, J. D. Cotter, and P. N. Ainsli; *Clin. Physiol. Funct. Imaging;* 2007, 27(4) (July), 211-216; and
9. Changes in the peripheral blood flow in legs in response to the cold: own studies using plethysmography; E. astowiecka-Moras, J. Bugajska, and Ireneusz Jurczak; *International Journal of Occupational Safety and Ergonomics,* 2016, 22:4, 501-507.
10. Calf muscle stimulation with the Veinoplus device results in a significant increase in lower limb inflow without generating limb ischemia or pain in patients with peripheral artery disease; P. Abraham, V. Mateus, F. Bieuzen, N. Ouedraogo, F. Cisse, and G. Leftheriotis, *Journal of Vascular Surgery,* 2013, 57(3) (March), 714-719;
11. Influence of transcutaneous electrical nerve stimulation on clinical measures and functional capacity in patients with peripheral artery disease; T. Pellinger, C. B. Pearce, and G. H. Simmons, *The Faseb Journal,* 2017, Volume 31, Supplement 1 Abstract Number:1015.35 (Apr. 1, 2017);
12. Non-invasive management of peripheral artery disease; K. J. Williams, A. Babber, R. Ravikumar, and A. H. Davies, *Adv. Exp. Med. Biol.* 2017, 906, 387-406.
13. The efficacy of transcutaneous electrical nerve stimulation on the improvement of walking distance in patients with peripheral artery disease with intermittent claudication: study protocol for a randomised controlled trial: the TENS-PAD study; F. Besnier, J. M. Sénard, V. Grémeaux, M. Riédel, D. Garrigues, T. Guiraud, and M. Labrunée, J., *Trials,* 2017, 18(1) (Aug. 10, 2017), 373;
14. Muscle electrostimulation: alternative of adjuvant treatment to patients with peripheral arterial obstructive disease; A. H. de Oliveira Medeirosm, S. T. Chalegrel, C. C. de Carvalho, *Jornal Vascular Brasileiro,* 2007, 6(2) (June 2007).

These current "passive" electro-stimulatory strategies to treat PAD contrast with the "active" treatment strategies for PAD treatments including behavioral changes such as smoking cessation, exercise, changes in diet, various drugs (e.g. antiplatelets and statins), and catheter-based or surgical interventions, some of which can be more risky and more costly than passive strategies. For some patients with advanced PAD, the only option is leg amputation.

What is not disclosed in these references is a diagnostic, monitoring, and treatment methodology that combines or integrates a thermally-based capillary blood flow methodology and device such as disclosed in U.S. Pat. No. 6,221,025, with a variable intensity stimulation methodology and device. Any of the disclosed stimulation types can be used in this combination of variable intensity stimulation and capillary blood flow measurement. When the stimulatory technology is a transcutaneous electrical neural stimulation, this synergistic combination is referred to as a VI-TENS (variable intensity transcutaneous electrical neural stimulation) plus CBF (Capillary Blood Flow) methodology and device or system, as further described below.

With the stimulation technologies described in the references above, a variety of different measuring or monitoring technologies can be used to measure blood flow changes, such as laser-Doppler flowmeter methods, Near Infrared (NIR), Far Infrared (FIR), various forms of plethysmography, and the like. However, it has been unexpectedly discovered that by integrating a thermally-based capillary blood flow methodology and device such as disclosed in U.S. Pat. No. 6,221,025, with a variable intensity stimulation methodology and device, a synergistic method and system are obtained which allow the diagnosis of vascular dysfunction in an accurate and cost-effective manner, including the early-stage diagnosis and treatment that was heretofore not available. This diagnosis can be used to detect vascular insufficiencies and when coupled with treatment, can be used to monitor and adjust the treatment.

In an aspect, the vascular dysfunction which can be detected, treated and monitored according to this disclosure can comprise an early stage disease condition or disease state. In another aspect, the vascular dysfunction comprises Peripheral Arterial Disease (PAD) or the earliest stages of disease progression of PAD.

According a further aspect, the vascular dysfunction also can derive from soft tissue injury. In one aspect of the disclosure, the vascular dysfunction may be associated with muscle damage, injury, or atrophy. Muscle atrophy can occur with prolonged immobility of individuals of all ages, and the present methods and systems can be used as convenient and cost effective means for monitoring and treatment with a view towards prevention.

In an aspect of this disclosure, it has been found that stimulation technologies, such as electrical stimulation, magnetic stimulation, infrared stimulation, ultrasound stimulation, and the like, which can provide and facilitate stimulation using a range of power or intensity levels over time can show a real-time correlative increase in the local capillary blood flow in healthy individual human subjects. This correlation has been discovered to contrast with corresponding tests in human subjects which may have incipient, developing, or fully developed vascular conditions impeding the capillary blood flow. In such individuals, stimulation technologies providing stimulation using a range of power or intensity levels over time typically will either show no correlative increase in the local capillary blood flow with power or intensity levels of stimulation, or they will be significantly less pronounced than in a healthy subject. As a result, a system and method have been developed that allows the early detection diagnostics for these individuals.

In embodiments and aspects, the stimulation technology can comprise transcutaneous electrical neural stimulation (TENS). Examples of devices utilizing TENS technology include but are not limited to Omron E2 Elite™ TENS device (and other similar Omron TENS devices) and the Veino Plus™ Sport Electrical Stimulator device. In the disclosed methodology and system, a DermaFlow (Perichek Multi™) peripheral (capillary) blood flow system was used for measuring capillary blood flow response using the combined methodology with the stimulation device. In an aspect, there is flexibility for the capillary blood flow system in its configuration. For example, the heater and the temperature sensor can be combined into a capillary blood flow sensor module. In an aspect, the heater comprises a silicon diode, the temperature sensor comprises a silicon diode, or both the heater and the temperature sensor can comprise a silicon diode. For example, the heater comprises a first silicon diode, the temperature sensor comprises a second silicon diode, and the first and second silicon diodes are arranged in a diode array and are electrically insulated from each other.

In an aspect, one embodiment of this disclosure is provided in Example 1 and in the data produced in this example as shown in FIG. 1. In Example 1, the DermaFlow (Perichek Multi™) capillary blood flow system was used for measuring capillary blood flow response, and the Omron E2 Elite™ TENS device was used for applying the stimulation at two or more different stimulation intensities at the area of interest in the subject. The TENS electrodes were placed on an extremity of the human subject, for example, on a calf muscle, the DermaFlow Perichek Multi™ sensor was placed in close proximity. Baseline peripheral blood flow measurements were initiated with the DermaFlow Perichek Multi™ device prior to applying any TENS stimulation, after which TENS stimulation was applied at multiple different power levels, while capillary blood flow measurements continued to be recorded. This variable power or variable intensity stimulation, referred to in this specific example as variable intensity transcutaneous electrical neural stimulation or VI-TENS, combined with continuous capillary blood flow (CBF) monitoring is described in detail in Example 1. FIG. 1 illustrates the stimulation intensity levels versus the change in peripheral blood flow rate of Example 1 and illustrates how the difference between baseline capillary blood flow and the stimulated capillary blood flows vary in relative units, as a function of the corresponding stimulation intensity in a healthy leg versus a Peripheral Arterial Diseased (PAD) leg.

Accordingly, in these aspects, there are provided a method of detecting vascular dysfunction in an extremity of a human body, and if desired, there is also provided a method of treating or prevention vascular dysfunction in an extremity of a human body. In an aspect, the method of detecting vascular dysfunction can comprise:

a) providing a capillary blood flow sensor comprising:
 i) a heater for applying heat to an area of skin to change the temperature of the skin from a first temperature to a second temperature and for maintaining a constant temperature gradient between the first and second temperatures, and a power source for providing a power to the heater; and
 ii) a temperature sensor for measuring the first temperature at the area of skin;

b) determining a capillary blood flow response to a stimulation in an upper or lower extremity by:
 i) in the absence of the stimulation, measuring a first temperature at an area of skin with the temperature sensor;
 ii) applying heat to the area of skin with the heater to change the first temperature to a second temperature and maintaining the temperature gradient constant;
 iii) measuring the heater power dissipation required to maintain the temperature gradient constant;
 iv) determining a baseline capillary blood flow as a function of the heater power dissipation based upon a linear relationship of the Fourier equation;
 v) applying the stimulation at two or more different stimulation intensities, for example increasing stimulation intensities, at the area of skin and determining two or more corresponding stimulated capillary blood flows as a function of the heater power dissipation based upon the linear relationship of the Fourier equation; and c) comparing the baseline capillary blood flow to each of the two or more stimulated capillary blood flows and determining a change in capillary blood flow as a function of the corresponding stimulation intensity to detect vascular dysfunction in the upper or lower extremity.

This disclosure also provides a method of treating or preventing vascular dysfunction in the extremity, as described herein.

In an aspect, the stimulation can be applied two or more times at different stimulation intensities. Detecting vascular dysfunction in the upper or lower extremity can be achieved by comparing the change in capillary blood flow from baseline flow (in the absence of stimulation) to stimulated flow at different stimulation intensities. That is, whether the stimulated capillary blood flow increases with increasing stimulation intensity reflecting healthy vascular flow, or whether capillary blood flow maintains relatively little or no change with increasing stimulation intensity reflecting a diseased or incipient diseased or compromised vascular flow can be observed. It is this combination of variable intensity stimulation with capillary blood flow monitoring that is particularly diagnostic.

According to a further aspect, the stimulation can be applied two or more times at different stimulation intensities. For example, the stimulation can be applied 2, 3, 4, 5, 6, 7, 8, 9, 10, 11, 12, 13, 14, 15, 16, 17, 18, 19, 20, or more times. Stimulation intensities can be applied across the full range of stimulation intensities available with the particular stimulation technology and associated apparatus. Detecting vascular dysfunction in the upper or lower extremity can be achieved by determining the correlation between the change in stimulated capillary blood flow as a function of the different stimulation intensities.

In an aspect, for example, a healthy individual will show an increasing blood flow as a function of increased intensity of stimulation, whereas an individual suffering from Peripheral Arterial Disease (PAD) will show a very small difference, if any, between the stimulated capillary blood flow as a function of increasing intensity of the of stimulation. Therefore, the slope of this correlation line, whether increasing significantly, increasing marginally as compared to a known healthy limb, not increasing at all, or even decreasing can be used as appreciated by the skilled person to assess the health of an upper or lower extremity of a patient. In a healthy subject, increasing intensity or power of the stimulation consistently increases blood flow. In a vascular compromised subject, only small (if any) blood flow changes as a function of increased stimulation intensity. In other words, the less the flow changes with increasing intensity stimulation, the more likely that the subject has vascular dysfunction.

Therefore, in an aspect of the method of detecting vascular dysfunction and in the method of treating or prevention vascular dysfunction in an extremity of a human body as disclosed herein, in the steps of comparing the baseline capillary blood flow to each of the two or more stimulated capillary blood flows and determining a change in capillary blood flow as a function of the corresponding stimulation intensity to detect vascular dysfunction in the upper or lower extremity, the following correlations can be made. In this aspect, when applying the stimulation occurs at three or more different stimulation intensities, if the slope of the change in capillary blood flow versus stimulation intensity trend line is continuously increasing, a diagnosis of a healthy extremity is indicated. If the slope of the change in capillary blood flow versus stimulation intensity trend line is not continuously increasing, a diagnosis of a diseased or pre-diseased extremity is indicated. Finally, if the slope of the change in capillary blood flow versus stimulation intensity trend line is decreasing, near zero, or zero, a diagnosis of a diseased extremity is indicated.

In an aspect, the stimulation can be applied at one or more selected stimulation intensities to determine one or more corresponding stimulated capillary blood flows, but the information provided by a single stimulation intensity by comparing it to an unstimulated capillary blood flow is substantially less informative for diagnosis than the change in stimulated capillary blood flow as a function of multiple different stimulation intensities. Generally, when more stimulation intensities are used in the disclosed methods, the diagnostic information obtained is more helpful in determining a trend and in diagnosing vascular insufficiencies.

In an aspect, this disclosure provides a method of detecting and treating or preventing vascular dysfunction in an extremity of a human body, in which the method can comprise:

a) providing a capillary blood flow sensor comprising:
  i) a heater for applying heat to an area of skin to change the temperature of the skin from a first temperature to a second temperature and for maintaining a constant temperature gradient between the first and second temperatures, and a power source for providing a power to the heater; and
  ii) a temperature sensor for measuring the first temperature at the area of skin;

b) determining a capillary blood flow response to a first stimulation in an upper or lower extremity by:
  i) in the absence of the first stimulation, measuring a first temperature at an area of skin with the temperature sensor;
  ii) applying heat to the area of skin with the heater to change the first temperature to a second temperature and maintaining the temperature gradient constant;
  iii) measuring the heater power dissipation required to maintain the temperature gradient constant;
  iv) determining a baseline capillary blood flow as a function of the heater power dissipation based upon a linear relationship of the Fourier equation;
  v) applying the first stimulation at two or more different first stimulation intensities at the area of skin and determining two or more corresponding stimulated capillary blood flows as a function of the heater power dissipation based upon the linear relationship of the Fourier equation;

c) comparing the baseline capillary blood flow to each of the two or more stimulated capillary blood flows and determining a change in capillary blood flow as a function of the corresponding first stimulation intensity to detect vascular dysfunction in the upper or lower extremity; and d) treating the vascular dysfunction if detected, for example by applying a second stimulation, or preventing the vascular dysfunction if not detected, for example by applying a second stimulation.

In this aspect, the first stimulation can be referred to as a "diagnostic" stimulation, and the second stimulation can be referred to as a "treatment" stimulation.

Therefore, in an aspect, the step of treating the vascular dysfunction can comprise utilizing a stimulation treatment regimen of applying a stimulation (that is, the second stimulation in the above method) one or more times to the upper or lower extremity at one or more selected second stimulation intensities, for one or more durations of time. The references listed above, each of which is incorporated herein by reference in its entirety, demonstrate various methods by which stimulation treatments and protocols can increase the peripheral blood flow in the capillaries. In one aspect, the second (treatment) stimulation type can be the same as the first (diagnostic) stimulation type. In another aspect, the second (treatment) stimulation type can be different from the first (diagnostic) stimulation type.

In the method for detecting and treating vascular dysfunction, the first stimulation can comprise transcutaneous electrical neural stimulation (TENS). The second stimulation also can comprise transcutaneous electrical neural stimulation (TENS). Both the first stimulation and the second stimulation can comprise transcutaneous electrical neural stimulation (TENS).

In an aspect, when the first stimulation, the second stimulation, or both the first and second stimulations comprise transcutaneous electrical neural stimulation (TENS), the step of applying the TENS stimulation can comprise the steps of:
 a) providing an electrical current waveform generator for generating an electrical stimulation signal, a controller for regulating the intensity of the electrical stimulation signal in communication with the electrical current waveform generator, one or more electrodes, and one or more leads, each lead in communication with the controller and a corresponding electrode;
 b) contacting the one or more electrodes with the area of skin; and
 c) initiating an electrical current stimulation signal through the one or more leads and into the tissue of the body, the controller regulating the electrical current stimulation signal at a selected intensity.

According to another aspect of this disclosure, there is provided a system for detecting vascular dysfunction in an extremity of a human body, in which the system can comprise a capillary blood flow module and a stimulation module, wherein
 a) the capillary blood flow module comprises:
  i) a heater for applying heat to an area of skin to change the temperature of the skin from a first temperature to a second temperature and for maintaining a constant temperature gradient between the first and second temperatures, and a power source for providing power to the heater;
  ii) a temperature sensor for measuring temperature at the area of skin;
  iii) a controller in communication with the heater and the temperature sensor which [A] operates the heater for maintaining the temperature gradient constant and [B] operates the temperature sensor in a first operative mode and a second operative mode, wherein
   in the first operative mode the temperature sensor measures the first temperature at the area of skin,
   and wherein in the second operative mode, the controller operates the heater to maintain the temperature gradient constant between the first and second temperatures;
  and
  iv) a processor in communication with the controller for determining a capillary blood flow units corresponding to the measured first temperature and the heater power required to maintain the temperature gradient constant; and
 b) the stimulation module comprises:
  i) an electrical current waveform generator for generating an electrical stimulation signal;
  ii) a controller for regulating the intensity of the electrical stimulation signal in communication with the electrical current waveform generator; and
  iii) at least one electrode and at least one lead, each lead in communication with the controller and a corresponding electrode.

The capillary blood flow module controller and the stimulation module controller can operate in a tandem, synergistic fashion to detect vascular dysfunction. Moreover, the functionality of the capillary blood flow module controller and the stimulation module controller can be integrated into single operating system if desired. The system or device can also include a display device in communication with the processor for visually displaying the measured capillary blood flow.

In accordance with this disclosure there is provided a system for detecting and treating or preventing vascular dysfunction in an extremity of a human body, in which the system can comprise a capillary blood flow module and a stimulation module, wherein
 a) the capillary blood flow module comprises:
  i) a heater for applying heat to an area of skin to change the temperature of the skin from a first temperature to a second temperature and for maintaining a constant temperature gradient between the first and second temperatures, and a power source for providing power to the heater;
  ii) a temperature sensor for measuring temperature at the area of skin;
  iii) a controller in communication with the heater and the temperature sensor which [A] operates the heater for maintaining the temperature gradient constant and [B] operates the temperature sensor in a first operative mode and a second operative mode, wherein
   in the first operative mode the temperature sensor measures the first temperature at the area of skin,
   and wherein in the second operative mode, the controller operates the heater to maintain the temperature gradient constant between the first and second temperatures;
  and
  iv) a processor in communication with the controller for determining a capillary blood flow units corresponding to the measured first temperature and the heater power required to maintain the temperature gradient constant; and
 b) the stimulation module comprises:
  i) an electrical current waveform generator for generating an electrical stimulation signal;
  ii) a controller for regulating the intensity of the electrical stimulation signal in communication with the electrical current waveform generator; and
  iii) at least one electrode and at least one lead, each lead in communication with the controller and a corresponding electrode;
wherein the stimulation module operates in tandem with the capillary blood flow module to detect vascular dysfunction.

In this aspect, the electrical stimulation signal can be applied two, three, four, five, six, seven, eight, nine, ten or more times at different stimulation intensities. Detecting vascular dysfunction in the upper or lower extremity can be achieved by comparing the change in capillary blood flow at different stimulation intensities.

The method and system disclosed herein provide different ways in which the stimulation can be used, that is, for detection and for treatment or prevention. In this aspect, treating or preventing the vascular dysfunction can comprise utilizing a stimulation treatment regimen of applying a stimulation one or more times to the upper or lower extremity, at one or more selected stimulation intensities, for one or more periods of time or stimulation durations. The type of stimulation used in treatment or prevention of vascular dysfunction can be the same as the stimulation type used in the diagnosis. Alternatively, the type of stimulation used in treatment or prevention of vascular dysfunction can be different from the stimulation type used in the diagnosis.

As used herein, a "second" stimulation is used to refer to the stimulation used when treating or preventing vascular dysfunction, whereas a "first" stimulation is used to refer to the stimulation used when diagnosing vascular dysfunction which is used in a synergistic method and system with measuring capillary blood flow. The second (treatment) stimulation typically utilizes different stimulation power, intensity, frequency, and time parameters from those used in the first (detection) stimulation.

If the vascular dysfunction is discovered based upon the tell-tale pattern between healthy versus diseased legs such as illustrated in FIG. 1, then there is provided a method of treating vascular dysfunction in an extremity of a human body, in which the method can comprise, following the method of detecting vascular dysfunction as described above, step d) of treating the vascular dysfunction according the various methods, including the method of providing another stimulation for treatment, which can be the same or different at the stimulation used to detect the vascular dysfunction in the detection phase. Even if vascular dysfunction is not discovered based upon the tell-tale pattern between healthy versus diseased legs such as illustrated in FIG. 1, then there is provided a method of preventing vascular dysfunction in an extremity of a human body, in which the method can comprise, following the method of detecting vascular dysfunction as described above, step d) of preventing the vascular dysfunction according to the various methods, including the method of providing another stimulation for treatment, which can be the same or different at the stimulation used to detect the vascular dysfunction in the detection phase.

As illustrated in FIG. 1, the healthy leg of the healthy individual shows an increasing blood flow as a function of increased intensity of transcutaneous electrical neural stimulation on the calf, while, that of the Peripheral Arterial Disease (PAD) diagnosed leg shows very small differences if any, as a function of increasing intensity. Some PAD-diagnosed legs may show decreases in capillary blood flow as a function of increasing intensity of the stimulation.

In addition to the ability to diagnose and treat diseased extremities based upon their differing discovered behaviors as explained above, an intermediate category of disease state or progression has been identified using the disclosed method and system, which can be classified as pre-diseased or early-stage disease states. Therefore, in another aspect, a further embodiment is provided in Example 2 and in the Example 2 data shown in FIG. 2, which demonstrates how this pre- or early-disease status can be visualized, detected and treated.

In Example 2, the same DermaFlow Perichek Multi™ capillary blood flow system and the Omron E2 Elite™ TENS device were used as provided in Example 1, however, data were measured on each calf muscle of both legs of the same human subject. The FIG. 2 data illustrate how the difference between baseline capillary blood flow and the trend in stimulated capillary blood flow using different stimulation intensities is capable of detecting and measuring early-stage PAD diseased extremities. Specifically, the FIG. 2 data compares one leg (right) which is Peripheral Arterial Diseased (PAD), while the other leg can be considered pre-PAD diseased but not disease-free, which can benefit from treatment at this early stage. The Peripheral Arterial Diseased diagnosis of the right leg was completed prior to and entirely independently of the measurements in this Example, by vascular physicians using the accepted standard methodologies (ABI and the like) currently used in vascular medicine.

In an aspect, these differing patterns can be analyzed by software algorithms and categorized either in gross terms (for example, healthy versus diseased) or may be correlated to quantitative scales currently used in Peripheral Arterial Disease (PAD), such as Ankle Brachial Index (ABI) as an example. Therefore, this disclosure also provides for algorithms based on the diagnostic patterns of stimulation intensity versus change in capillary blood flow, which can provide information on whether an extremity shows disease, incipient disease, or no disease. In one aspect, by using multiple stimulation intensities and monitoring changes in capillary blood flow as a function of intensity, the trend in capillary blood flow change can be analyzed using various algorithms to provide a quantitative measure of the extent of disease or injury. For example, an algorithm can analyze the slope of the stimulation intensity versus change in capillary blood flow line or trend. When the algorithm detects a positive slope in which the capillary blood flow increases with increasing intensity, the algorithm can provide an analysis of a healthy extremity. When the algorithm detects a zero, near zero, or negative slope in which the capillary blood flow increases with increasing intensity, the algorithm can provide an analysis of a diseased or early stage diseased extremity.

In an aspect, the variable intensity stimulation such as VI-TENS plus capillary blood flow (CBF) method and device may be incorporated into wearable or portable type devices for convenience and prolonged monitoring. Such devices may be paired with, for example, an app for the mobile phone, which can be used to provide real time data. Moreover, the tandem or integrated variable intensity stimulation (for example, VI-TENS) plus CBF device, method or capability may be used together with currently available ABI technologies.

In a further aspect, the variable intensity stimulation, in particular VI-TENS, plus CBF methodology can form the basis of a device comprising both those technologies in an integrative format to be used routinely in at least the following ways. In one aspect, a VI-TENS plus CBF combined device and method can be used for screening symptomatic as well as asymptomatic populations for PAD. The convenience, ease and speed of screening would be particularly helpful in patient compliance in the screening process, particularly for asymptomatic individuals. Home monitoring of PAD disease for those who have been already diagnosed, or those in high risk categories for disease maintenance, can be effected in a convenient and cost effective manner using the methodology and system of this disclosure. Similarly, home treatment is provided conveniently and inexpensively for increasing blood flow, and monitoring this treatment with automation and modulation variations can be accomplished with relative ease as understood by the skilled person. In a further aspect, the augmentation of mobility and the prevention of vascular insufficiencies as a result of increased blood flow can be accomplished, including with the home monitoring and treatment or prevention methods and systems provided herein.

In addition to the early detection and treatment of compromised blood flow due to disease or conditions developed as a result of unhealthy lifestyle and/or genetics, injury to the lower limbs can also result in "temporary" compromised blood flow to the injured muscle. Injury occurs often with athletes and in sports related activities, and the variable intensity stimulation plus CBF device and method are also effective at diagnosis, monitoring and screening in injury-related vascular dysfunction, for example to monitor the efficacy of treatments. In an aspect, it has been demonstrated that stimulation of injured appendages, together with monitoring peripheral blood flow can confirm compromised capillary blood flow and hence the injury and its healing progress can be monitored either on its own or in an enhanced manner using any number of stimulation types or modalities discussed above.

The majority of the complications relating to muscle injuries originate in the hematoma of the injury, which may increase in size and cause compartment syndrome, or it may evolve into an encapsulated hematoma. There may be rupture or loosening of the muscle fascia, which enables extravasation of part of the muscle belly through the opening in the fascia, thus causing pain and functional abnormalities. If the patient also has an infection at another site, there may be contamination, which then may give rise to the need for surgical drainage. The methods and systems of this disclosure provide a means to monitor the healing process, can potentially prevent further medical complications, and can provide improved healthcare management of the injury in both athletes and non-athlete patients.

Figure 3:
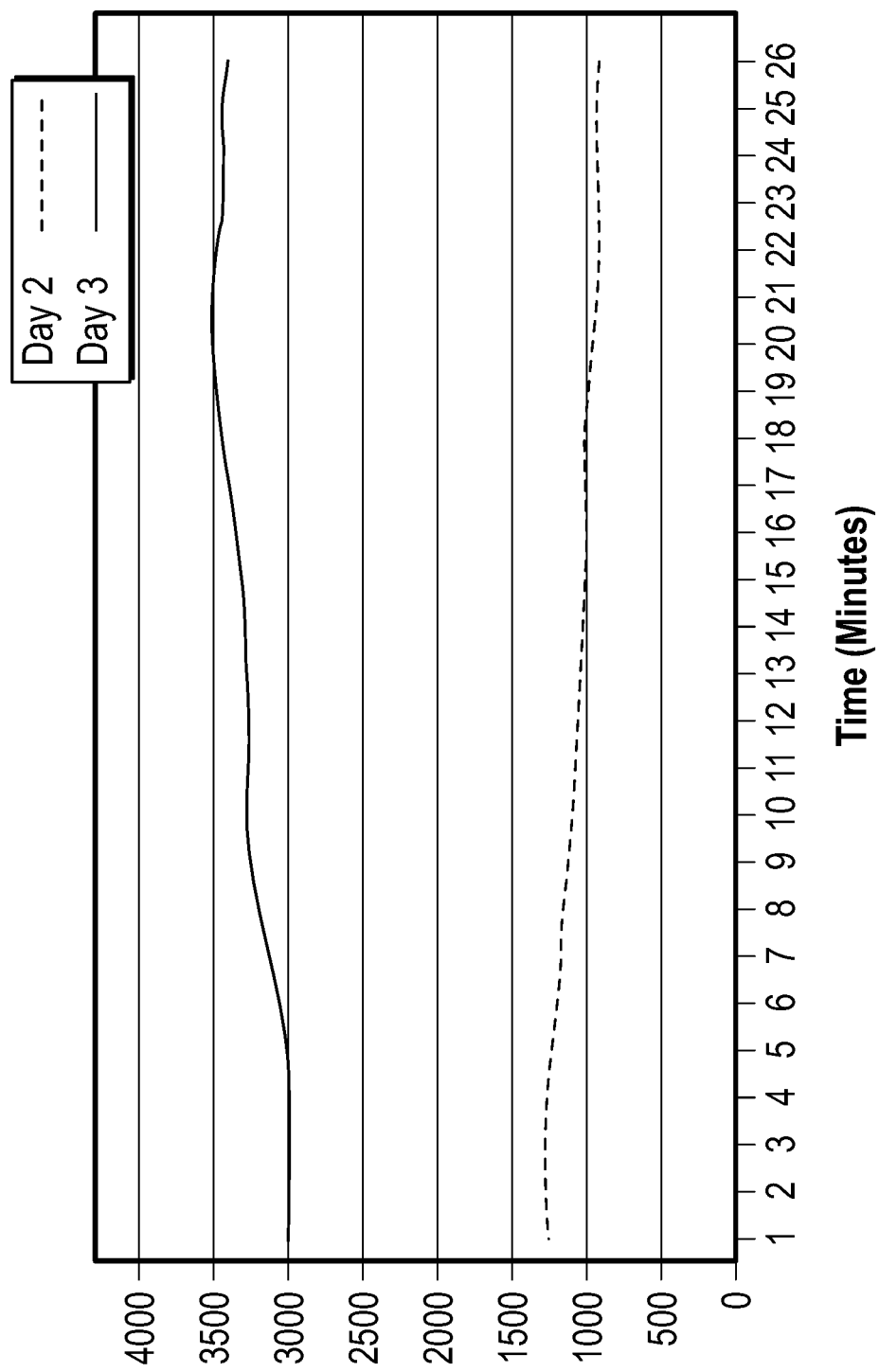
FIG. 3 illustrates a further embodiment of the disclosure in which the method and system are in the diagnostic mode to track the results based upon the healing progression.

An embodiment of this aspect is provided in Example 3 and in the data produced in this example shown in FIG. 3. In Example 3, an athlete with a first degree lower leg muscle injury has been monitored with thermal-based capillary blood flow (CBF) in coordinated or integrated fashion with an electrical stimulation (which is not variable intensity). In this example, the combined stimulation plus CBF methodology is used on an injured calf muscle of an athlete, using a Veino Plus™ stimulation device plus a DermaFlow Perichek Multi™ device for detection and monitoring of healing. Baseline peripheral blood flow measurements were initiated with the DermaFlow Perichek Multi™ device prior to applying the Veino Plus™ stimulation, wherein the instrument was activated to apply a low voltage and a low frequency stimulation, while capillary blood flow measurements continued to be recorded.

FIG. 3 plots the data for Example 3, specifically the time of each measurement in minutes using the Veino Plus™ Sport electrical stimulator (x-axis) versus the relative change in peripheral blood flow rate. This figure reflects healing over time, using the same stimulatory intensity during measurements, therefore, intensity and power are kept constant in this test, and no changes in frequency (bpm) are employed. In the FIG. 3 data, it is seen that the trend of the two lines is informative. The capillary blood flow along the y-axis of FIG. 3 is a relative scale. Data were collected following a muscle injury at two days after the injury (bottom plot, lower relative flow rate) and at three days after the injury (top plot, higher relative flow rate). The day 2 data (bottom line) show a diminishing capillary blood flow trend with increasing time. The day 3 data (top line) demonstrate an increasing capillary blood flow trend with increasing time, providing evidence of healing as the capillary blood flow at day 3 as reflected in this increasing capillary blood flow trend suggesting a more healthy tissue resulting from healing progression.

Therefore, one aspect of this disclosure provides a method for monitoring the healing of a soft tissue injury in an extremity of a human body, the method comprising:

a) providing a capillary blood flow sensor comprising:
  i) a heater for applying heat to an area of skin to change the temperature of the skin from a first temperature to a second temperature and for maintaining a constant temperature gradient between the first and second temperatures, and a power source for providing a power to the heater; and
  ii) a temperature sensor for measuring the first temperature at the area of skin;

b) determining a capillary blood flow response to a stimulation at an injury in an upper or lower extremity by:
  i) in the absence of the stimulation, measuring a first temperature at an area of skin at the injury with the temperature sensor;
  ii) applying heat to the area of skin with the heater to change the first temperature to a second temperature and maintaining the temperature gradient constant;
  iii) measuring the heater power dissipation required to maintain the temperature gradient constant;
  iv) determining a baseline capillary blood flow as a function of the heater power dissipation based upon a linear relationship of the Fourier equation;
  v) applying a stimulation at a single stimulation intensity at the area of skin and determining the stimulated capillary blood flows as a function of time and a function of the heater power dissipation based upon the linear relationship of the Fourier equation; and c) comparing the baseline capillary blood flow to the stimulated capillary blood flows and determining a change in capillary blood flow as a function of time to detect vascular dysfunction in the upper or lower extremity.

In an aspect, combined variable intensity stimulation plus CBF methodology can form the basis for a routine and inexpensive portable or wearable device which can both monitor and treat appendage injury in all populations. In a further aspect, the combined variable intensity stimulation plus CBF methodology can be used to great advantage for athletes for diagnosing, monitoring, and treating injury, and for preventing re-injury due to a return to athletic endeavors too soon after the injury.

Therefore, particularly useful embodiments of this aspect of the variable intensity stimulation, for example, VI-TENS, plus CBF methodology which provides feedback regarding dynamic changes in capillary blood flow can include, for example: (1) stimulation treatments to be modulated based on monitoring results; (2) automation of wearable forms of such a variable intensity stimulation (e.g. VI-TENS) plus CBF device; (3) better assessment of when an athlete can return to sports participation; (4) more efficient physical therapy programs for injured athletes; and (5) implications for health/injury insurance for athletes.

Therefore, in various aspects there are provided at least the following: (1) a methodology and device comprising a stimulation technology used cooperatively with monitoring capillary blood flow for early detection and treatment of compromised circulation; (2) use of trans-cutaneous electronic neural stimulation or similar electro-stimulation in an aspect of the disclosed methodology and device; (3) use of other types of trans-cutaneous stimulation such as ultrasound, magnetic, infrared, mechanical vibration, thermal, and the like, including combinations thereof in an aspect of the disclosed methodology and device; (4) use of the DermaFlow thermal technology for monitoring capillary blood flow in an aspect of the disclosed methodology and device; (5) early detection of Peripheral Arterial Disease (PAD) and associated treatment thereof in an aspect of the disclosed methodology and device; and (6) monitoring capability for healing status of a muscle injury in an aspect of the disclosed methodology and device.

EXAMPLES

The invention is further illustrated by the following examples, which are not to be construed in any way as imposing limitations to the scope of this invention. Various other aspects, embodiments, modifications, and equivalents thereof which, after reading the description herein, can suggest themselves to one of ordinary skill in the art without departing from the spirit of the present invention or the scope of the appended claims.

General Experimental Procedures. Measurements using a DermaFlow Perichek Multi™ were taken as disclosed in U.S. Pat. No. 6,221,025. Because the methods of this disclosure use differences between capillary blood flow between non-stimulated measurements versus measurements stimulated at various intensities, which are accurate and convenient to obtain, it was not necessary to calibrate the capillary blood flow system in absolute flow units as disclosed in PCT Patent Application No. PCT/US2018/044369. However, a capillary blood flow system that has been calibrated in absolute flow units can be used if desired.

In Examples 1 and 2, a DermaFlow (Perichek Multi™) peripheral (capillary) blood flow system was used for measuring capillary blood flow response and an Omron E2 Elite™ Trans-Cutaneous Electronic Neural Stimulation (TENS) device was used for applying the stimulation at multiple selected stimulation intensities at the area of interest. Example 3 used a DermaFlow (Perichek™ Demo) capillary blood flow system for measuring capillary blood flow response and a Veino Plus™ Sport (Electrical Stimulator) device for applying the stimulation at a single stimulation intensity at the area of interest over time. Unless otherwise provided, the capillary blood flow module (sensor) and the stimulation instrument or module were used in tandem mode in which the capillary blood flow controller and the stimulation controller were operated in a coordinated fashion as described herein.

The DermaFlow Perichek Multi™ capillary blood flow system was used for the measurements of these examples. In an aspect, there is flexibility for the capillary blood flow system in its configuration. For example, the heater and the temperature sensor can be combined into a capillary blood flow sensor module. In an aspect, the heater can comprise a silicon diode, the temperature sensor comprises a silicon diode, or both the heater and the temperature sensor can comprise a silicon diode. For example, the heater comprises a first silicon diode, the temperature sensor comprises a second silicon diode, and the first and second silicon diodes are arranged in a diode array and are electrically insulated from each other.

Figure 2:
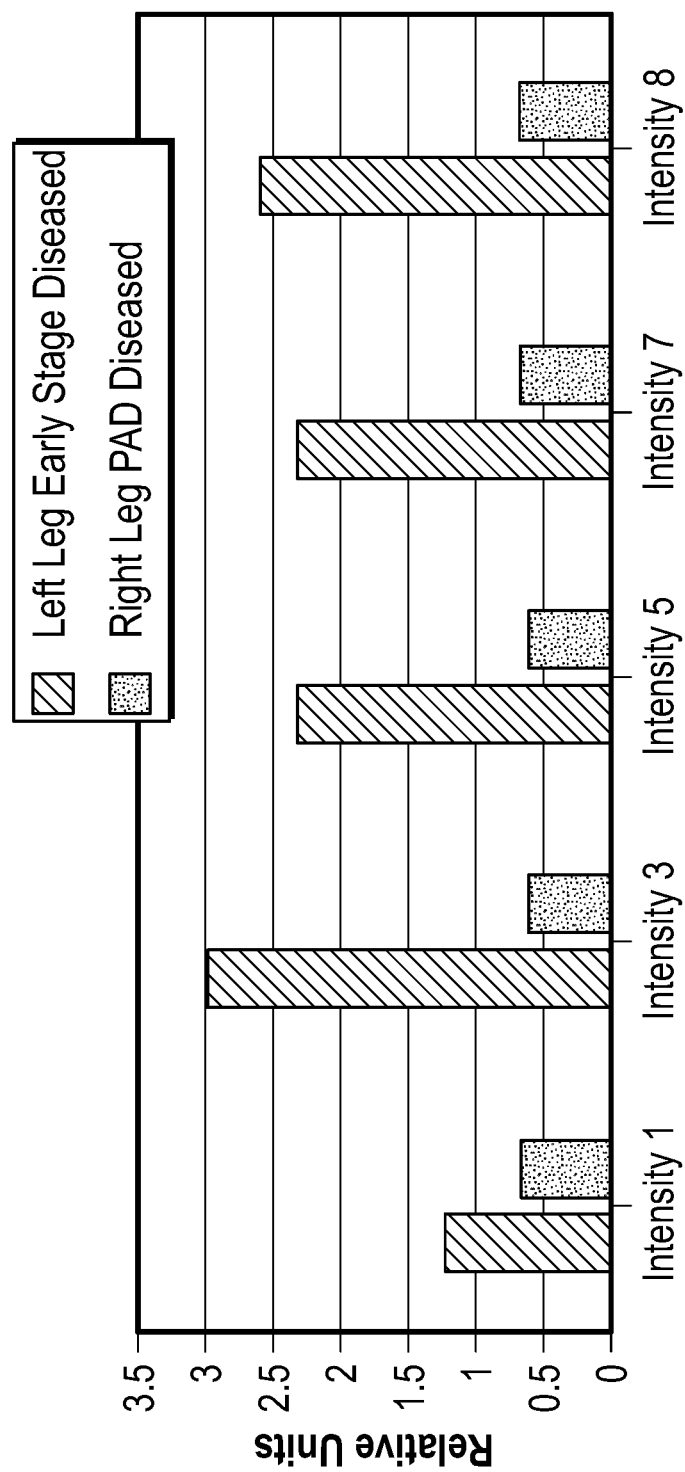
FIG. 2 illustrates another embodiment of the disclosure and also plots the stimulation intensity versus the change in peripheral blood flow rate using transcutaneous electrical neural stimulation (TENS) as the stimulation method. These data were measured on each calf muscle of both legs of the same human subject and illustrate how the difference between baseline capillary blood flow and the stimulated capillary blood flows vary in relative units, as a function of the corresponding stimulation intensity. This plot compares one leg (right) which is Peripheral Arterial Diseased (PAD), while the other leg can be considered pre-PAD diseased and not disease-free, which can be observed by comparison with the FIG. 1 plot. The intensity level of a Trans-Cutaneous Electronic Neural Stimulation (Omron E2 Elite) is shown along the x-axis.

Referring to FIGS. 1-3 which correspond with Examples 1-3, the relative units in FIG. 3 and Example 3 are taken directly from an arbitrary scale built into the capillary blood flow software of the DermaFlow Perichek Multi™ capillary blood flow system, which extends from 0 to 10,000. After calibration, measurements were initiated, which usually were started near the middle of this arbitrary scale. In FIG. 1 (Example 1) and FIG. 2 (Example 2), the calculated changes in capillary blood flow were calculated based on values from the same arbitrary scale as used in FIG. 3 (Example 3), however, these large values are normalized or standardized to a more convenient scale by determining what capillary blood flow change (A, based on the initial arbitrary values) occurs in a healthy individual, when going from baseline to Intensity 1. Normalizing this change A as equal to the value 1 and comparing all other changes to this $\Delta=1$ provides the values shown in FIG. 1 and FIG. 2.

Example 1

In Examples 1 and 2, a DermaFlow (Perichek Multi™) peripheral (capillary) blood flow system was used for measuring capillary blood flow response. An Omron E2 Elite™ Trans-Cutaneous Electronic Neural Stimulation (TENS) device was used for applying the stimulation at two or more different stimulation intensities at the area of interest. Unless otherwise provided, the Perichek Multi™ capillary blood flow instrument and the Omron E2 Elite™ TENS instrument were used in tandem mode in which the capillary blood flow controller and the stimulation controller were operated in a coordinated fashion.

On all subjects measured, the following protocol was used. Subjects were at rest, sitting comfortably in a chair with their legs placed on the floor in a natural manner. The two TENS electrodes of the Omron E2 Elite™ TENS instrument were placed on the subject to be measured, with one electrode placed on the subjects' calf and one electrode placed on the subjects' ankle. In close proximity to but not touching the TENS electrodes, the DermaFlow Perichek Multi™ sensors were placed on the subjects' legs, one on the calf and one on the ankle.

The DermaFlow Perichek Multi™ power source and sensors were activated and baseline measurements of capillary blood flow were taken at least 5 minutes prior to applying the TENS stimulation to obtain an accurate baseline capillary blood flow measurement. After obtaining baseline capillary blood flow data for the patient, the Omron E2 Elite™ instrument was activated to apply a TENS stimulation, while capillary blood flow measurements continued to be taken with the DermaFlow Perichek Multi™ instrument.

The Omron E2 Elite™ device is designed with 10 different intensity settings (indicated as 1 to 10). A first capillary blood flow measurement was taken while the Omron E2 Elite™ device at an intensity of 1 was used. Subsequent capillary blood flow measurements were taken while the Omron E2 Elite™ device was set at intensity levels of 3, 5, and 7. The following stimulation and time sequence was used during the measurement: 4 minutes at intensity 1; 6 minutes at intensity 3; 10 minutes at intensity 5; and 10 minutes at intensity 7. During this stimulation and time sequence, the DermaFlow Perichek Multi™ device continued to measure capillary blood flow at each sensor location. The capillary blood flow data was exported using the dedicated DermaFlow software and plotted in graphical format as the amount of change in peripheral flow measured as a function of applied TENS intensity, normalized as explained above.

FIG. 1 plots the stimulation intensity versus the change in peripheral blood flow rate of Example 1, using data measured on the calf muscle of the legs of different human subjects. This plot illustrates how the difference between baseline capillary blood flow and the stimulated capillary blood flow varies in relative units, as a function of the corresponding stimulation intensity in a healthy leg versus a Peripheral Arterial Diseased (PAD) leg.

Example 2

The general details of Example 2 are described in Example 1. The DermaFlow Perichek Multi™ and the Omron E2 Elite™ instruments were used to measure capillary blood flow and apply a TENS stimulation, in the manner described in Example 1. Again, TENS stimulation was applied while capillary blood flow measurements continued to be collected with the DermaFlow Perichek Multi™ instrument. The same stimulation and time sequence from Example 1 was used during the measurement: 4 minutes at intensity 1; 6 minutes at intensity 3; 10 minutes at intensity 5; and 10 minutes at intensity 7.

FIG. 2 plots the stimulation intensity versus the change in peripheral blood flow rate of Example 2, using data that were measured on each calf muscle of both legs of the same human subject and illustrate how the difference between baseline capillary blood flow and the stimulated capillary blood flow varies in relative units, as a function of the corresponding stimulation intensity, and is capable of observing and measuring early-stage PAD diseased extremities. This data compares one leg (right) which is Peripheral Arterial Diseased (PAD), while the other leg can be considered pre-PAD diseased but not disease-free.

Example 3

Example 3 used a DermaFlow (Perichek™ Demo) capillary blood flow system for measuring capillary blood flow response and a Veino Plus™ Sport (Electrical Stimulator) device for applying the stimulation at a single stimulation intensity at the area of interest. Unless otherwise provided, the capillary blood flow module (sensor) and the stimulation module or instrument were used in tandem mode in which the capillary blood flow controller and the stimulation controller were operated in a coordinated fashion to provide the synergistic measurements, even though they were under independent control.

On all subjects measured, the following protocol was used. Human subjects were athletes and were situated at rest, lying down comfortably on their stomachs with their calf muscles exposed in an upward fashion. The DermaFlow sensor was placed in the center of the calf muscle and held in place by a sports band to provide a hermetic seal against the skin. The two Veino Plus™ electrodes were placed one above the calf and one below the calf.

The DermaFlow sensors were activated and baseline measurements of capillary blood flow were taken at least 5 minutes prior to applying the Veino Plus™ stimulation to obtain an accurate baseline capillary blood flow measurement. After obtaining baseline capillary blood flow data for the subject, the Veino Plus™ instrument was activated to apply a low voltage and a low frequency stimulation, while capillary blood flow measurements continued to be taken with the DermaFlow capillary blood flow instrument. The Veino Plus™ provided electrical stimulation while using a constant medium intensity, in range of about 50 beats per minute (bpm) (on a scale from 0 to about 150 bpm). Stimulation was continuous and uninterrupted during the measurements, and capillary blood flow measurements were continuously monitored, and data are reported each minute.

Data from Example 3 are illustrated at FIG. 3, which shows the time of the capillary blood flow measurement in minutes during continuous use of the Veino Plus™ Sport electrical stimulator (x-axis) versus the relative change in capillary blood flow rate. Intensity is kept constant in this test, and no changes in frequency (bpm) are employed. In the FIG. 3 data, it is seen that the trend of the two lines is informative. The capillary blood flow along the y-axis of FIG. 3 is a relative scale. Data were collected following a muscle injury at two days after the injury (bottom plot, lower relative flow rate) and at three days after the injury (top plot, higher relative flow rate). The day 2 data (bottom line) show a diminishing capillary blood flow trend with increasing stimulation time. The day 3 data (top line) demonstrate an increasing capillary blood flow trend with increasing stimulation time, providing evidence of healing as the capillary blood flow at day 3 as reflected in this increasing capillary blood flow trend suggesting a more healthy tissue resulting from further healing progression.

Aspects of this disclosure are further set out in the following claims. Many variations will suggest themselves to those skilled in the art in light of the above detailed description. All such obvious variations are within the full intended scope of the appended claims. Other aspects of the invention can include, but are not limited to, the following aspects. Many aspects or embodiments are described as "comprising" certain components or steps, but alternatively, can "consist essentially of" or "consist of" those components or steps unless specifically stated otherwise.

What is claimed is:

1. A method for detecting vascular dysfunction in an extremity of a human body, the method comprising:
   a) providing a capillary blood flow sensor comprising:
      i) a heater for applying heat to an area of skin to change a temperature of the skin from a first temperature to a second temperature and for maintaining a constant temperature gradient between the first and second temperatures, and a power source for providing a power to the heater; and
      ii) a temperature sensor for measuring the first temperature at the area of skin;
   b) determining a capillary blood flow response to a first (diagnostic) stimulation in an upper or lower extremity by:
      i) in the absence of the first stimulation, measuring the first temperature at an area of skin with the temperature sensor;
      ii) applying heat to the area of skin with the heater to change the first temperature to a second temperature and maintaining the temperature gradient constant;
      iii) measuring the heater power dissipation required to maintain the temperature gradient constant:
      iv) determining a baseline capillary blood flow as a function of the heater power dissipation based upon a linear relationship of the Fourier equation;
      v) applying the first stimulation at two or more different first stimulation intensities at the area of skin and determining two or more corresponding stimulated capillary blood flows as a function of a heater power dissipation based upon the linear relationship of the Fourier equation; and
   c) comparing the baseline capillary blood flow to each of the two or more stimulated capillary blood flows and determining a change in capillary blood flow as a function of the corresponding first stimulation intensity to detect the vascular dysfunction in the upper or lower extremity.

2. A method according to claim 1, wherein the first stimulation comprises electrical stimulation, magnetic stimulation, infrared stimulation, ultrasound stimulation, mechanical vibration stimulation, thermal stimulation (heat or cold), or any combination thereof.

3. A method according to claim 1, wherein the first stimulation comprises transcutaneous electrical neural stimulation (TENS).

4. A method according to claim 3, wherein applying the transcutaneous electrical neural stimulation (TENS) comprises the steps of:
   a) providing an electrical current waveform generator for generating an electrical stimulation signal, a controller for regulating an intensity of the electrical stimulation signal in communication with the electrical current waveform generator, one or more electrodes, and one or more leads, each lead in communication with the controller and a corresponding electrode;
   b) contacting the one or more electrodes with the area of skin; and
   c) initiating an electrical current stimulation signal through the one or more leads and into tissue of the body, the controller regulating the electrical current stimulation signal at a selected intensity.

5. A method according to claim 1, wherein the first stimulation is applied at from 3 to 15 different first stimulation intensities, and from 3 to 15 corresponding stimulated capillary blood flows are determined.

6. A method according to claim 1, wherein applying the first stimulation occurs at three or more different first stimulation intensities, and:
   a) if the slope of the change in capillary blood flow versus the first stimulation intensity trend line is continuously increasing, a diagnosis of a healthy extremity is indicated;
   b) if the slope of the change in capillary blood flow versus the first stimulation intensity trend line is not continuously increasing, a diagnosis of a diseased or pre-diseased extremity is indicated; and
   c) if the slope of the change in capillary blood flow versus the first stimulation intensity trend line is decreasing, near zero, or zero, a diagnosis of a diseased extremity is indicated.

7. A method according to claim 1, wherein the heater and the temperature sensor are combined into a capillary blood flow sensor module.

8. A method according to claim 1, wherein the heater, the temperature sensor, or both the heater and the temperature sensor comprise(s) a silicon diode.

9. A method according to claim 1, wherein the heater comprises a first silicon diode, the temperature sensor comprises a second silicon diode, and the first and second silicon diodes are arranged in a diode array and are electrically insulated from each other.

10. A method according to claim 1, wherein the vascular dysfunction comprises an early stage disease condition.

11. A method according to claim 1, wherein the vascular dysfunction comprises: Peripheral Arterial Disease (PAD) pre-PAD; derives from soft tissue injury; or is associated with muscle damage, injury, or atrophy.

12. A method according to claim 1, further comprising treating the vascular dysfunction.

13. A method according to claim 12, wherein treating the vascular dysfunction comprises utilizing a stimulation treatment regimen of applying a second (treatment) stimulation one or more times to the upper or lower extremity at one or more selected second stimulation intensities, for one or more durations of time, wherein the second (treatment) stimulation type is the same as the first (diagnostic) stimulation type.

14. A method according to claim 12, wherein treating the vascular dysfunction comprises utilizing a stimulation treatment regimen of applying a second (treatment) stimulation one or more times to the upper or lower extremity at one or more selected second stimulation intensities, for one or more durations of time, wherein the second (treatment) stimulation type is different from the first (diagnostic) stimulation type.

15. A method according to claim 12, wherein treating the vascular dysfunction comprises utilizing a stimulation treatment regimen of applying a second (treatment) stimulation one or more times to the upper or lower extremity at one or more selected second stimulation intensities, for one or more durations of time, wherein the stimulation treatment regimen is different from the step of applying the first (diagnostic) stimulation to detect vascular dysfunction.

16. A method according to claim 12, wherein the second (treatment) stimulation comprises electrical stimulation, magnetic stimulation, infrared stimulation, ultrasound stimulation, mechanical vibration stimulation, thermal stimulation (heat or cold), or any combination thereof.

17. A method according to claim 12, wherein the second (treatment) stimulation comprises transcutaneous electrical neural stimulation (TENS).

18. A system for detecting and optionally treating vascular dysfunction in an extremity of a human body, the system comprising a capillary blood flow module and a stimulation module, wherein
   a) the capillary blood flow module comprises:
      i) a heater for applying heat to an area of skin to change a temperature of the skin from a first temperature to a second temperature and for maintaining a constant temperature gradient between the first and second temperatures, and a power source for providing power to the heater;
      ii) a temperature sensor for measuring temperature at the area of skin;
      iii) a controller in communication with the heater and the temperature sensor which [A] operates the heater for maintaining the temperature gradient constant and [B] operates the temperature sensor in a first operative mode and a second operative mode, wherein
         in the first operative mode the temperature sensor measures the first temperature at the area of skin, and wherein in the second operative mode, the controller operates the heater to maintain the temperature gradient constant between the first and second temperatures;
   and
      iv) a processor in communication with the controller for determining a capillary blood flow units corresponding to the measured first temperature and a heater power required to maintain the temperature gradient constant; and
   b) the stimulation module comprises:
      i) an electrical current waveform generator for generating an electrical stimulation signal;
      ii) a controller for regulating the intensity of the electrical stimulation signal in communication with the electrical current waveform generator; and
      iii) at least one electrode and at least one lead, each lead in communication with the controller and a corresponding electrode.

19. A system according to claim 18, wherein the capillary blood flow module controller and the stimulation module controller operate in tandem to detect vascular dysfunction.

20. A system according to claim 18, wherein functionality of the capillary blood flow module controller and the stimulation module controller are integrated into single operating system.

21. A system according to claim 18, wherein the heater, the temperature sensor, or both the heater and the temperature sensor comprise(s) a silicon diode.

22. A system according to claim 18, wherein the heater comprises a first silicon diode, the temperature sensor comprises a second silicon diode, and the first and second silicon diodes are arranged in a diode array and are electrically insulated from each other.

23. A system according to claim 18, further comprising a display device in communication with the processor for visually displaying the measured capillary blood flow units.

24. A system according to claim 18, wherein the heater and the temperature sensor are combined into capillary blood flow sensor module.

25. A method for monitoring the healing of a soft tissue injury in an extremity of a human body, the method comprising:
  a) providing a capillary blood flow sensor comprising:
    i) a heater for applying heat to an area of skin to change a temperature of the skin from a first temperature to a second temperature and for maintaining a constant temperature gradient between the first and second temperatures, and a power source for providing a power to the heater; and
    ii) a temperature sensor for measuring the first temperature at the area of skin;
  b) determining a capillary blood flow response to a stimulation at an injury in an upper or lower extremity by:
    i) in the absence of the stimulation, measuring the first temperature at an area of skin at the injury with the temperature sensor;
    ii) applying heat to the area of skin with the heater to change the first temperature to the second temperature and maintaining the temperature gradient constant;
    iii) measuring a heater power dissipation required to maintain the temperature gradient constant;
    iv) determining a baseline capillary blood flow as a function of the heater power dissipation based upon a linear relationship of the Fourier equation;
    v) applying a stimulation at a single stimulation intensity at the area of skin and determining a stimulated capillary blood flows as a function of time and a function of the heater power dissipation based upon the linear relationship of the Fourier equation; and
  c) comparing the baseline capillary blood flow to the stimulated capillary blood flows and determining a change in capillary blood flow as a function of time to detect vascular dysfunction in the upper or lower extremity.

* * * * *